(12) United States Patent
Quong (10) Patent No.: US 6,365,189 B1
(45) Date of Patent: *Apr. 2, 2002

(54) METHOD OF DELIVERING AND RELEASING A PHEROMONE

(75) Inventor: Douglas Quong, London (CA)

(73) Assignee: 3M Innovative Properties Company, St. Paul, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/426,140

(22) Filed: Oct. 22, 1999

(51) Int. Cl.[7] ............... A61K 9/14; A61K 9/50
(52) U.S. Cl. .......... 424/489; 424/499; 424/500
(58) Field of Search ............... 424/489, 493, 424/488, 500, 499

(56) References Cited

U.S. PATENT DOCUMENTS

| | | | |
|---|---|---|---|
| 3,577,515 A | 5/1971 | Vandegaer | 424/32 |
| 3,691,140 A | 9/1972 | Silver | 260/78.5 |
| 4,230,809 A | 10/1980 | Heinrich et al. | |
| 4,439,488 A | 3/1984 | Trmnell et al. | 428/402.24 |
| 4,487,759 A | 12/1984 | Nesbitt et al. | 424/32 |
| 4,532,123 A | 7/1985 | Gardner | 424/21 |
| 4,557,755 A | 12/1985 | Takahashi et al. | |
| 4,689,293 A | 8/1987 | Goosen et al. | 435/1 |

(List continued on next page.)

FOREIGN PATENT DOCUMENTS

| | | |
|---|---|---|
| CA | 1044134 | 12/1978 |
| CA | 1179682 | 12/1984 |
| EP | 0 371 635 | 7/1996 |
| JP | S 58-183601 | 10/1983 |
| JP | S 59-139301 | 8/1984 |
| JP | S 60-252403 | 12/1985 |
| JP | 5238957 | 2/1992 |
| JP | 4310233 | 11/1992 |
| JP | 10182320 | 12/1996 |
| JP | 9012447 | 1/1997 |
| JP | H 9-124408 | 5/1997 |
| WO | WO 98/44912 | 10/1998 |
| WO | WO 98/45036 | 10/1998 |

OTHER PUBLICATIONS

Gåserød, O. et al., "Microcapsules of alginate–chitosan. II. A study of capsule stability and permeability", Biomaterials, GB, Elsevier Science Publishers BV., Barking, vol. 20, pp. 773–793 (Apr. 1999).

Thu, B. et al., "Alginate polycation micrcapsules, II. Some functional properties", Biomaterials, GB, Elsevier Science Publishers BV., Barking, vol. 17, No. 11, pp. 1069–1079 (1996).

D. Quong, "DNA encapsulation within membrane coated alginate beads," Dept of Chemical Engineering, McGill University, Montreal, Canada, Jul. 1997.

Primary Examiner—Thurman K. Page
Assistant Examiner—Rachel M. Bennett
(74) Attorney, Agent, or Firm—Arlene L. Hornilla; Dale A. Bjorkman (57) ABSTRACT

A microbead having a matrix core comprising a hydrophilic matrix and droplets of active material entrained therein, and a secondary layer adjacent to the outer surface of the matrix core. The secondary layer may be ionically complexed or hydrogen bonded to the matrix core surface. Compositions comprising the microbeads suspended in solution may be sprayable. The microbeads of the invention may be controllable by exposing the microbeads to high or low humidity or moisture.

12 Claims, 1 Drawing Sheet

U.S. PATENT DOCUMENTS

| | | |
|---|---|---|
| 4,701,326 A | 10/1987 | Nelsen et al. ................ 424/408 |
| 4,746,513 A | 5/1988 | Smith |
| 4,755,377 A | 7/1988 | Steer ......................... 424/76.4 |
| 5,045,569 A | 9/1991 | Delgado ...................... 521/63 |
| 5,089,606 A | 2/1992 | Cole et al. .................... 536/54 |
| 5,183,690 A * | 2/1993 | Carr et al. ............. 427/213.31 |
| 5,427,935 A * | 6/1995 | Wang et al. ................. 435/178 |
| 5,508,313 A | 4/1996 | Delgado et al. ............... 521/60 |
| 5,635,609 A | 6/1997 | Levy et al. ..................... 536/2 |
| 5,645,844 A | 7/1997 | Henderson et al. ......... 424/405 |
| 5,786,216 A * | 6/1998 | Dionne et al. .............. 435/402 |

\* cited by examiner

Figure 1:
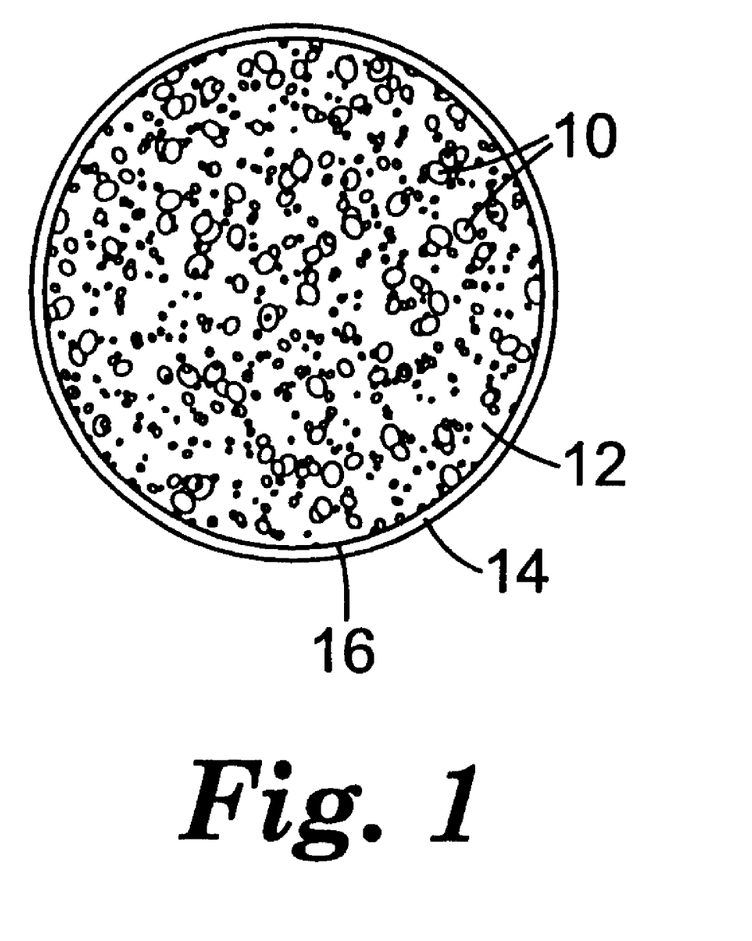

*Fig. 1*

METHOD OF DELIVERING AND RELEASING A PHEROMONE subsequent polymerization of monomers from each phase at the interface between the bulk (continuous) phase, and the dispersed droplets. Polyurethanes and polyureas are materials suitable for producing the microcapsules. The microcapsules comprise a polymeric sphere and a liquid centre, ranging from 30 micron to 2 mm in diameter, depending on monomers and solvents used.

Highly viscous and thickened hydrogels have been used to deliver pheromones, fragrances and other non-water soluble actives. U.S. Pat. No. 4,755,377, for example, describes a process of encapsulating perfume or fragrant material within an aqueous-based gel composition. The resulting material is in the form of a highly viscous semi-solid. U.S. Pat. No. 5,645,844 describes the use of chitosan paste for delivery of pheromones to disrupt insect mating, where the material can be dispensed by an apparatus such as a caulking gun. Due to their thickness and high viscosity, these materials, however, are generally unsprayable compositions.

Most hydrogels are safe and non-toxic to humans. Hydrogels are have been used for the encapsulation of biological materials whereby the formulation is non-lethal to the viability of the cells, proteins, and related materials. U.S. Pat. No. 4,689,293, describes the process of encapsulating living tissue or cells in alginate beads. The encapsulation shell permits the passage of materials and oxygen to the cells and permits the diffusion of the metabolic by-products from the gel. In U.S. Pat. No. 5,635,609, the encapsulation art described involves one esterified polysaccharide (i.e., alginate) and one polyamine (i.e. chitosan) whereby the outer surface membranes are formed through covalent amide bonds. U.S. Pat. No. 4,439,488 teaches a process of encapsulating pheromone whereby the biological agents are dissolved or dispersed in an aqueous paste of a gel-forming polyhydroxy polymer. By adding boric acid to an alkaline pH, the paste transforms into a gel thereby entrapping the agents in a protective matrix.

Japanese patent S 60-252403 describes a method of forming sprayable, slow release pheromone agent obtained by emulsification co-polymerization. In Japanese patent H-9-1244-08, the outer surface of the delivery system (i.e., synthetic resin or inorganic substance) is coated by a water-proof material. The water-proof agent can be a silicon, fluroine, or paraffin hydrogen carbide type material.

SUMMARY OF THE INVENTION

A method of delivering active material using a plurality of microbeads suspended in solution is provided, where the microbeads comprise a hydrophilic matrix having droplets of active material entrained therein and a secondary layer adjacent to the surface of the matrix. Furthermore, the matrix is capable of immobilizing a broad spectrum of active materials, either water soluble or non-water soluble. In one aspect of the invention, the hydrophilic matrix may be made from a naturally occurring material to provide an environmentally friendly microbead.

In an aspect of the invention, the active entrained in the matrix diffuses through the hydrophilic matrix and the secondary layer, and is released into the environment over an extended period.

In another aspect, the microbeads are capable of re-hydrating after an initial dehydration and release of active. Thus, the release and longevity of the active can be controlled by adjusting the humidity of the environment in which the microbeads have been delivered.

BRIEF DESCRIPTION OF THE DRAWINGS

FIG. 1 is a cross-sectional illustration depicting a preferred embodiment of a microbead of the invention.

DETAILED DESCRIPTION OF THE PREFERRED EMBODIMENTS

In view of the increasing awareness of insecticide toxicity to humans and other environmental concerns, it would be advantageous to provide an active delivery system having an extended release life and having a hydrogel material in order that it be non-toxic and bio-degradeable. It would also be advantageous to provide a system for sprayable long lasting active delivery that would be applicable to a broad spectrum of actives thereby eliminating the issue of reactivity of the active with one of the membrane components.

The present invention provides microbeads having a secondary layer, where the microbeads are made of a hydrophilic matrix core having droplets of active material entrained and immobilized therein. Surprisingly, it has been found that release of the active from within the microbeads can be altered by adding a secondary layer onto the microbead surface to alter the diffusion pathway of the active and subsequently extend and improve the active release properties. Furthermore, the secondary layer advantageously provides physical protection to the hydrogel matrix with the active entrained therein, from rupturing forces, UV, and other external environmental conditions.

The secondary layer can be a membrane, web, coating, film, or other material that is positioned outside and adjacent to the outer surface of the matrix core. For simplicity, the term "secondary" layer is used herein to describe the layer that lays immediately outside the surface of the matrix core. Thus, it is contemplated, that the microbeads of the invention can have multiple layers.

The microbeads of the invention comprise a matrix forming material, and is preferably substantially spherical. The matrix forming materials of the microbead core are hydrophilic and water soluble. Entrained or finely dispersed within the matrix are micro-sized droplets of active material. Active materials that can be immobilized within the hydrogel microbeads include acetates, aldehydes, alcohols, esters, epoxy compounds, ethers, and ketones, especially reactive ketones in which the double bond of the carbonyl group is conjugated with one or more double bonds, for example acetophenone where the carbonyl group is conjugated with double bonds of the aromatic ring.

Advantageously, the hydrogel matrix core is preferably made from environmentally or biologically friendly materials to provide sufficient immobilization of oil soluble actives such that the active can be delivered and sprayed by conventional techniques. By utilizing a hydrophilic matrix core, the hydrogel microbeads entrap micro-sized droplets of active material within the matrix. This is in contrast to delivery systems that solely utilize microencapsulation of actives, achieved by interfacial condensation. Immobilizing active material in a hydrophilic matrix core advantageously imparts the capability of the hydrogel microbeads to immobilize oil-soluble active materials and minimizes the risk of undesired reactivity between the active and its immobilizer. Thus, immobilization of active materials by use of the microbeads of the invention does not render the immobilized material inert or ineffective.

It has also been surprisingly found that the microbeads of the invention provide a method of controlling release of active(s) by cyclically hydrating and re-hydrating the microbeads. This is a result of the surprising benefit from immobilizing active ingredients in hydrogel microbeads, where the microbead is able to "swell" under humid conditions and shrink under dry conditions. As used herein, "swell" is descriptive of the behavior of a microbead, wherein the size (volume) is enlarged (increased) due to absorption of water. The microbeads' ability to swell is likely due to the hydrophilic nature of the matrix forming materials used to immobilize the active material.

In the presence of humidity, the hydrogel microbeads are surprisingly found to be capable of absorbing moisture, rehydrating, and consequently releasing active material contained within the microbead. This behavior can be cyclical. Thus, by controlling the humidity (or dryness) of the ambient air, the release rate of active material from the microbeads can be controlled such that specific periods of release can be generally predicted. It is therefore possible with the present invention to release the active material on demand from the microbead. Release on demand, or "smart release," can be advantageous in those instances where release is preferred at certain times. The microbeads' ability to release more active out from the matrix may increase the longevity of the release period. Preferably, the microbeads are delivered to an intended environment in effective amounts to obtain the desired effect. For example, microbeads having pheromones entrained therein, are preferably delivered to a desired area in amounts such that mating disruption is effected and release is accomplished for more than 4 weeks, more preferably, the microbead can release for more than about 6 weeks; and most preferably more than about 8 weeks.

During the drying process (i.e dehydration) a surface film layer will form as a result of water evaporation from the hydrophilic matrix. Both initially and during use, the microbeads are characterized by a large surface area to volume ratio, which helps maintain the rate of diffusion of the active material during use. Thus, it has been found that microbeads made according to the method of present invention provide excellent delivery systems as they are capable of releasing active material for extended periods. Furthermore, since the active is dispersed within a water-based matrix, additional protection from environmental conditions (i.e., UV) can be provided.

Although it has been found that microbeads of the invention can be made having a diameter of up to about 5 millimeters (mm), it is preferred that the microbeads be between about 1 micrometers ($\mu$m) to about 1000 $\mu$m and more preferably between about 1 $\mu$m to about 500 $\mu$m in diameter to ensure that the microbeads are easily sprayable from conventional spray nozzles. Most preferably, to ensure minimal clogging in conventional nozzles, the microbeads are less than about 400 $\mu$m in diameter. It is contemplated, however, that with the advent of larger spray nozzles not yet realized in the industry, the microbeads can be provided in much greater diameters.

For spraying applications, particularly aerial spraying, it is desirable that the microbeads be capable of remaining suspended in solution (e.g., water) to ensure that the microbeads do not sink, settle, or coagulate in the suspension. A uniform suspension ensures an even spray coverage. Preferably, the microbeads of the invention are able to remain in suspension, thus minimizing if not eliminating the need to agitate during application (and storage). Various suspension aids can also be included in the suspension containing the microbeads of the invention. Examples of suitable suspension aids include rhamsam gum, xanthum gum, gellan gum, pectin, and gum arabic.

Owing to the handling to which the microbeads are subjected, it is desirable that the microbeads of the present invention should be somewhat elastic, and not frangible. For example, typical atomization of a suspension during a spray application will force the suspension through two rotating perforated discs that are immediately upstream of the discharge nozzle. Sufficient elasticity of the microbeads minimizes physical damage to the microbeads as they pass through the discs.

The microbeads of the present invention comprise a hydrophilic matrix core having active material droplets entrained therein, and a secondary layer adjacent matrix forming material and active material. Referring now to FIG. 1, a preferred embodiment is shown, where a plurality of active material droplets 10 is entrained within the hydrogel matrix 12, and a layer 14 adjacent to outer surface 16 of the matrix 12. As seen in FIG. 1, active material droplets are preferably located between and within the hydrogel matrix, where the matrix provides an immobilizing network around the droplets. The degree and extent of agitation as well as the type of surfactant used to form the microbeads can affect the size and the dispersity of the pheromone droplets within microbead's matrix. Droplets are preferably between about 0.01 nm to about 200,000 nm in diameter. More preferably, the droplets are between about 1 to about 1000 nm.

The matrix-forming material useful in the present invention are biocompatible, water-soluble, have pendant functional groups, and complex with ions (e.g., polyvalent cations and/or anions) to form hydrogels. Functional groups of the matrix forming material include for example, carboxyls, hydroxyls, primary or secondary amines, aldehydes, ketones, esters, or combinations thereof. Preferably, the matrix-forming material of the hydrophilic matrix core can be made from natural occurring polysaccharides, such as alginates, chitosans, gums, agars, carrageenans, or the matrix can be made synthetic, water soluble monomers, oligomers or polymers, such as, for example, polyvinyl alcohol, poly(N-isoproylacrylamide), acrylamides, acrylates, methacrylates or combinations thereof.

Suitable naturally occurring polysaccharides include the water-soluble salts of alginic, pectic and hyaluronic acids, the water-soluble salts or esters of polyglucuronic acid, polymanuronic acid, polylygalacturonic acid and polyarabinic acid, and gum kappa-carrageenan. The preferred polysaccharides are the ammonium, magnesium, potassium, sodium and other alkali metal salts of alginic acid, and the most preferred polysaccharide is sodium alginate.

"Alginate" is the general name given to alginic acid and its salts. Alginates are composed of D-mannosyluronic (mannuronic-"M") and L-gulopyranosyluronic (guluronic-"G") acid residues. The ratio of mannuronic to guluronic acid residues is known as the M:G ratio. The alginate used to immoblize active droplets should be carefully selected to ensure proper microbead formation, ensure the stability of the microbeads during storage and delivery applications, and ensure that the microbeads are able to shrink and swell appropriately to deliver the desired active material over an extended period of time (preferably 4–6 weeks). Preferably, an alginate is chosen such that the matrix formed is sufficient in strength to withstand the shear forces (conditions) placed upon the microbeads during application via a spray nozzle— i.e., the microbeads are resistant to rupture during the spray application.

For strength and stability of the microbeads, it is desirable to choose a proper molecular weight of the alginate, as well as an appropriate M:G ratio. Although alginates high in mannuronic acid are generally useful for thickening applications, whereas alginates with a high level of guluronic acid are often used for forming gels, both alginate categories (individually or a mixture thereof) are suitable for the microbeads of the invention. A preferred alginate that imparts strength and rupture resistance is an alginate that has a high level of guluronic acid, e.g., greater than about 30 percent by weight. Alginate compositions with excessive levels of mannuronic acid could result in less stable and less rigid microbeads than high guluronic acid gels. However, high mannuronic acid alginates impart to the microbeads the capability of swelling and absorbing more water than microbeads of high guluronic acid content. Thus, a careful balance of the advantages imparted by each of M and G residues should be considered when choosing a suitable alginate.

It has been surprisingly found that alginates preferably having a molecular weight in the range of about 100,000 kg/mol to about 2,500,000 kg/mol, more preferably about 200,000 kg/mol to about 1,500,000 kg/mol. Furthermore, the alginates preferably have an M:G ratio in the range of about 0.2 to about 3.5; more preferably about 0.3 to about 1.85.

Suitable alginates that have a high level of guluronic acid, for example are alginates from the algae *Laminaria hyperborea*, stem, whole plant or frond. Preferred alginates with high levels of mannuronic acid include *Ascophyllum nodosum*, for example.

Gel matrices formed by crosslinking polysaccharides bearing pendant carboxylate groups are also useful in the present invention. These compounds are composed of water-insoluble alginates which include, with the exception of magnesium and the alkali metal salts, the group II metal salts of alginic acid. The water-insoluble alginate gels are typically formed by the chemical conversion of water-soluble alginates, in an aqueous solution, into water-insoluble alginates. This conversion usually is accomplished by the reaction of a water-soluble alginate with polyvalent cations released from a soluble di- or trivalent metal salt.

Water-soluble alginates can include the ammonium, magnesium, potassium, sodium, and other alkali metal salts of alginic acid. Water-insoluble di- or trivalent metal salts suitable for the present invention should satisfy two requirements: (1) that the water-insoluble metal salt contain a di-or trivalent metal ion capable of complexing with the pendant carboxylate groups of the water-soluble polysaccharide to cause the formation of a water-insoluble polysaccharide gel; and (2) that the water-insoluble metal salt reacts with a water-soluble acid to form a water-soluble metal salt.

A common and suitable alginate gel is composed of calcium aliginate.

Sources for the crosslinking calcium ions used in the formation of alginate gels include, for example, calcium carbonate, calcium sulfate, calcium chloride, calcium phosphate, calcium tartrate, calcium nitrate, and calcium hydroxide. Other acceptable crosslinkers may include lanthanum chloride, ferric chloride, cobaltous chloride, as generally are other compounds with multivalent cations, such as calcium (Ca++), copper (Cu++), barium (Ba++), strontium (Sr++) and the like.

The time of gelation of the calcium alginate gels can be accomplished by regulating the concentration of free calcium ions in the solution. Typically the concentration of free calcium ions is controlled by manipulation of the ionization rate of the calcium salt and/or by the inclusion of other compounds in the solution which react with the free calcium ions.

It has been advantageously found that it is possible to immobilize and deliver a wide range of active materials, including non-water soluble materials as well as alcohols.

Preferred active materials entrained in the matrix core are partially water-miscible organic molecules of compounds that have a molecular weight in the range of between about 100 to about 400, preferably between about 150 to 300. The compounds contain a heteroatom that confers some degree of water-miscibility. For many compounds of interest the sole heteroatom is oxygen, and there may be up to three heteroatoms per molecule in, for instance, hydroxy-substituted or keto-substituted carboxylic acids. Unsubstituted carboxylic acids of course contain two oxygen atoms and simple aldehydes, ketones and ethers contain only one oxygen atom. Compounds that contain nitrogen and/or sulphur atoms are also of interest.

Of particular interest are biologically active compounds. For purposes of the present invention, the term "biologically active" means materials that affect the life processes of organisms. Materials that are biologically active include herbicides, pesticides, pharmaceuticals, and semiochemicals, including naturally and artificially produced pheromones and synthetic pheromone analogs. Materials of this nature that are of particular interest are those materials that interfere with a life process essential to the survival of a target pest.

The method of the invention can be used to immobilize pheromone with functional groups such as acetates, aldehydes, ketones, alcohols, esters, ethers, epoxies or combinations thereof. Pheromones may be defined as compounds which, when naturally produced, are secreted by one member of an animal species which can influence the behaviour or development of another member of the same animal species. Pheromones generally are species-specific and therefore the application of pheromones for insect behaviour modification has minimal effect on non-target pests. Pheromones supplied for modification of insect behaviour interfere with the "mate finding process" by releasing point sources of pheromone, which may compete with or camouflage the pheromone plume of a female. This latter type of action differs from chemical insecticides or insect growth regulators or hormones, in that pheromones target future generations of insects, not present ones. As pheromones are very species-specific and are used only in small quantities, their use is more environmentally acceptable than broadcasting of pesticides.

Many pheromones have an ester terminal group, for example and acetate or formate group. Typically these substances are water-immiscible and incorporation of them into microcapsules by known methods presents no particular problem. Many other pheromones have an aldehyde or an alcohol terminal group. In general, these are partially water-miscible and potentially reactive with the reactants used to encapsulate by prior, conventional methods. In particular, it is difficult to achieve high degrees of encapsulation of materials that have some degree of water solubility, as the material partitions between the small amount of organic solvent and the relatively larger amount of water that constitutes the continuous phase. Furthermore, these compounds can be expected to react with the reactants used to encapsulate. Aldehydes and ketones react with amines to form aldimines and ketimines, respectively. Alcohols, carboxylic acids and mercaptans react with isocyanates. Epoxy compounds react both with amines and with isocyanates. Thus, the present invention overcomes the limitation of delivering partially water-miscible substances such as alcohols, aldehydes, carboxylic acids, ketones, ethers, including epoxy compounds, and mercaptans.

Pheromones useful in the inventive microbeads are preferably insect pheromones. In describing the structure of the a pheromone, the following notation is used: the type (E (trans) or Z(cis)) and position of the double bond or bonds are given first, the number of carbon atoms in the chain is given next and the nature of the end group is given last. To illustrate, the pheromone Z-10 C19 aldehyde has the structure;

Pheromones can be mixtures of compounds with one component of the mixture predominating, or at least being a significant component. Partially water-miscible significant or predominant components of insect pheromones, with the target species in brackets, include, for example: E/Z-11 C14 aldehyde (Eastern Spruce Budworm), Z-10 C19 aldehyde (Yellow Headed Spruce Sawfly), Z-11 C14 alcohol (Oblique Banded Leafroller), Z-8 C12 alcohol (Oriental Fruit moth) and E,E-8,10 C12 alcohol (Codling moth), E-11 C14 acetate (Sparganothis Fruitworm), and Z-11 C14 acetate (Blackheaded Fireworm).

An example of a ketone that is a pheromone is E or Z 7-tetradecen-2-one, which is effective with the oriental beetle. An ether that is not a pheromone but is of value is 4-allylanisole, which can be used to render pine trees unattractive to the Southern pine beetle.

Preferred embodiments of the invention are described with reference to immobilization of partially water-miscible and water immiscible pheromones, but it should be appreciated that the invention extends to immobilization of materials other than such pheromones and to microbeads containing materials other than pheromones. Those materials may, or may not, be biologically active.

For example, alternatively, active materials containing mercaptans can be immobilized in the microbeads of the invention, such as what is found in urine of animals. These compounds are preferable in situations where animals mark their territory by means of urine, to discourage other animals from entering the particular territory. Examples of such animals include preying animals such as wolves, lions, dogs, etc. By dispersing hydrogel microbeads containing the appropriate mercaptans, it is possible to define a territory and discourage particular animals from entering that territory. For example, the urine of a wolf includes a mercaptan, and distribution of microbeads from which this mercaptan is gradually released to define a territory will discourage deer from entering that territory. Other active materials useful in discouraging approach of animals include essences of garlic, putrescent eggs and capsaicin.

Other active compounds that can be included in the microbeads of the invention include perfumes, fragrances, flavouring agents and the like.

Optionally, oil absorbents can be incorporated into the active droplets. These absorbents can help retain the active droplets within the microbeads, resulting in longer lasting formulations. Clays and starches could also be used for this purpose.

The concentration of active material in the microbeads of the invention should be at a level such that the matrix forming material can still provide a strong, rupture resistant network and deliver an effective amount of the active material to the environment to which it is intended. Thus, the active material is preferably present in an amount between about 0.1 wt % to about 60 weight percent (wt %) of the total weight of the microbead. More preferably, the amount of active material is present in the microbead at between about 0.2 wt % to about 40 wt %; and most preferably between about 0.3 wt % to about 20 wt %.

Microbeads of the invention comprise at least one layer (hereinafter referred to as a "secondary layer") adjacent to the outer surface of the hydrophilic matrix core. To provide diffusion and release of the active into the atmosphere, the secondary layer can be a discontinuous layer, or alternatively, a continuous layer permeable to liquid (moisture). The secondary layer that is applied onto the microbead surface can be performed by chemical processes such as ionic complexation or alternatively in-situ polymerization which involves hydrogen bonding of the layer to the matrix core. It is preferable that the material used to form the secondary layer is chosen such that the path of diffusion of the active material is altered to provide extended release of the active. Suitable materials that can be used for the secondary layer include hydrophilic, hydrophobic, inorganic or organic materials or combinations thereof. Preferably, the secondary layer is biocompatible and easily biodegradeable in the environment.

In a preferred aspect, the secondary layer can be ionically complexed with the outer surface of the hydrophilic matrix core. Advantageously, an ionically complexed layer provides a different permeability and diffusion profile of the active through the secondary layer, than that of a secondary layer that is covalently bonded to a matrix core. The permeability and diffusion of the actives delivered by the compositions and methods of the invention provide extended release periods.

Formation of the secondary layer by ionic complexation is achieved by binding opposing charged groups (i.e. negatively-charged groups and positively-charged groups) of the matrix core materials and the secondary layer. Thus, the selection of the material to form the secondary layer depends on the surface charge of the hydrophilic matrix core. If the hydrophilic matrix core is comprised of a negatively charged hydrophilic material, then the counter charged material should be a positively-charged material, and vice-versa.

Negatively charged groups suitable for use in the invention, include for example, hydroxyl, carboxyl, sulphate, and phosphate groups. Preferred biocompatible negatively-charged hydrophilic materials include, for example a polysaccharide. Suitable polysaccharides include, for example, an alginate, a carrageenan, in particular kappa-carrageenan, a gelable pectin, in particular a low methoyxyl pectin, agar, gellan gum, or combinations thereof.

Positively-charged hydrophilic materials suitable for use in the invention include, for example, proteins, polylysines, polypeptide, polyamino acids, polysaccharide bearing amino groups such as chitosan and carboxymethyl cellulose, aliphatics, alicyclic or aromatic organic substances bearing several primary or secondary amino groups, such as ethylenediamine, hexamethylenediamine, piperazine, phenylenediamine, polyethyleneimine, poly(hexamethylene co-guanidine), or poly(methylene co-guanidine), or combinations thereof. Of these, chitosan and co-guanidine-containing compounds are particularly preferred. Chitosan, obtained by the deacetylation of chitin, is an amino-polysaccharide and a biopolymer widely distributed in nature. Chitosan is a linear polysaccharide composed of β-1,4 linked D-glucosamine residues. In nature, the polymer is partially acetylated, and it includes a wide range of polymers corresponding to various proportions of D-glucosamine and N-acetyl-glucosamine residues. The properties of chitosan in solution depend on molecular weight, the degree of deacetylation, pH and ionic strength.

The ionic complexation reaction generally requires an aqueous solvent. The concentration of the solute (acid or alkaline) is preferably about 0.01 wt % to about 10 wt %, more preferably about 0.05 wt % to about 4 wt %. The solvent is preferably chosen, and its pH adjusted, to avoid precipiation yet ensure satisfactory complexation of the counter-charges materials. For example, in a preferred embodiment where chitosan solution is used to complex with an alginate, the pH is preferably between about 1.0 and 6.0, more preferably between about 5.0 and 6.0.

The concentration of the secondary layer forming material is preferably about 0.01 wt % to about 10.0 wt %, more preferably about 0.02 wt % to 4.0 wt % based on the total solution weight.

In another preferred aspect, the secondary layer can be adjacent to and hydrogen bonded to the outer surface of the hydrophilic matrix core. This method is performed in-situ, where the secondary layer is deposited onto the surface of the hydrophilic matrix core. Alternatively, the in situ formation of a secondary layer may be formed by a reaction between a water-immiscible polyisocyanate and a water-miscible polyfunctional amine. The polyisocyanate may be dispersed within the hydrogel forming emulsion mixture or dissolved in or within the active droplet. Layers formed by the in situ methods can be continuous and preferably permeable. Suitable materials for use in the in-situ method include for example, polyurea, polyurethane, or polyureamethylene urea.

The polyisocyanate may be aromatic or aliphatic and may contain two, three or more isocyanate groups. Examples of aromatic polyisocyanates include 2,4- and 2,6-toluene diisocyanate, naphthalene diisocyanate, diphenylmethane diisocyanate and triphenylmethane-p,p',p"-trityl triisocyanate.

Aliphatic polyisocyanates may optionally be selected from aliphatic polyisocyanates containing two isocyanate functionalities, three isocyanate functionalities, or more than three isocyanate functionalities, or mixtures of these polyisocyanates. Preferably, the aliphatic polyisocyanate contains 5 to 30 carbons. More preferably, the aliphatic polyisocyanate comprise one or more cycloalkyl moieties. Examples of preferred isocyanates include dicyclohexylmethane-4,4'-diisocyanate; hexamethylene 1,6-diisocyanate; isophorone diisocyanate; trimethyl-hexamethylene diisocyanate; trimer of hexamethylene 1,6-diisocyanate; trimer of isophorone diisocyanate; 1,4-cyclohexane diisocyanate; 1,4-(dimethylisocyanato) cyclohexane; biuret of hexamethylene diisocyanate; urea of hexamethylene diisocyanate; trimethylenediisocyanate; propylene-1,2-diisocyanate; and butylene-1,2-diisocyanate. Mixtures of polyisocyanates can be used.

Particularly preferred polyisocyanates are polymethylene polyphenylisocyanates of formula wherein n is 2 to 4. These compounds are available under the trade-mark Mondur-MRS. The mole equivalent ratio of total primary amine functionality to isocyanate functionality in the system is preferably about 0.8:1 to 1:1.2, and more preferably about 1:1.1.

The polyfunctional amine, in the amount used, is preferably freely soluble in the water present in the reaction mixture.

The polyfunctional compound containing amine and/or hydroxy functional groups may contain at least two functional groups selected from primary amine, secondary amine and hydroxy groups. Examples of suitable compounds include ethylene diamine, diethylene triamine and compounds of the general formula wherein m takes a value from 1 to 8, and each R is independently hydrogen or methyl. Also useful are compounds whose structure is similar to the above formula, but which have one or more oxygen atoms present in ether linkages between carbon atoms. It is preferred that R is hydrogen, especially at the terminal amino groups. Aromatic diamines, for example toluene diamine, can be used. Mixtures of polyfunctional compounds can be used. Tetraethylene pentamine (TEPA) and pentamethylene hexamine are particularly preferred.

A suitable amine for use in this invention is trimethylamine, a tertiary amine. This compound, and its $C_2$, $C_3$ and $C_4$ homologues can be used in the microbeads of the invention. Other suitable tertiary amines include those containing a mixture of alkyl groups, for instance methyl diethylamine. The tertiary amine can contain more than one tertiary amine moiety. It may also contain other functional groups provided that those other functional groups do not interfere with the required reaction, or the functional groups participate beneficially in the required reaction. As an example of a functional group that does not interfere there is mentioned an ether group. As examples of groups that participate beneficially there are mentioned primary and secondary amine groups, which will form urea moieties with isocyanate groups, and hydroxyl groups, which will form urethane moieties with isocyanate groups. Examples of suitable tertiary amines include compounds of the following structures:

Of the tertiary amines triethyl amine (TEA) is preferred.

In another aspect of the in situ formation of the secondary layer, a water-insoluble non-thermoplastic synthetic resin may be used. Polymerization of the resin generally requires a pre-polymer. Prepolymers suitable to the present invention 
are partially etherified urea-formaldehyde prepolymers with a high solubility in the organic phase and low solubility in water. In its non-etherified form, the prepolymer contains a large number of methylol groups, —CH$_2$OH, in its molecular structure. Etherification is the replacement of the hydroxyl hydrogens with alkyl groups; and is preferably achieved by condensation of the prepolymer with an alcohol. Complete etherification is preferably avoided, however, since hydroxyl groups are needed for the in situ self-condensation polymerization, which occurs in the layer forming step. The secondary layer of this invention may comprise a water-soluble urea resin where at least one of the prepolymers is a mixture of formaldehyde and at least one compound selected from the group consisting of urea, melamine and thiourea.

The microbeads of the present invention can be placed into suspension in aqueous or solvent-based solutions. For environmental and biologically-friendly reasons, it is preferred that aqueous suspensions be used. Suspension aids are preferably included in the suspension formulations to ensure the microbeads remain suspended in solution.

Preferably, the suspension solution is substantially free of monovalent cations, such as sodium, to avoid degradation or breakdown of the secondary layer or the hydrogel matrix. In a preferred aspect, a concentration of approximately 50 millimolar of a crosslinker such as calcium chloride is maintained in a stored solution comprising the microbeads of the invention.

Optionally, adhesive material can be included in the compositions of the invention. The adhesive material can be provided in various forms, such as for example, latex or a tacky microspheres. Adherent properties imparted to the hydrogel microbeads should result in the microbeads being able to still retain their suspended state and minimize aggregation or coagulation in the aqueous suspension. Furthermore, any adhesive material used to impart adherent properties should not affect the integrity of the particles; it should not dissolve or weaken the microbeads.

A suitable adhesive material that may be included in the compositions of the invention is adhesive latex. The adhesive latex may be any suitable water-dispersible adhesive available in the art. In the agricultural business, such latex compositions are often called stickers or spreaders. Stickers are used to help non-encapsulated agriculture chemicals adhere to plants. Spreaders are used to help disperse non-encapsulated agriculture chemicals on application. Preferred adhesives are acrylate-based adhesives. One suitable latex is available from Rohm & Haas under the trade-mark Companion. Another is available from Deerpoint Industries under the trade-mark DPI S-100 (a proprietary sticker/spreader). Examples of such adhesives are polymers made from the “soft” monomers such as n-butyl acrylate, isooctyl acrylate, or the like, or copolymers made from a soft component, such as isobutylene, n-butyl acrylate, isooctyl acrylate, ethyl hexyl acrylate, or the like; and a polar monomer such as acrylic acid, acrylonitrile, acrylamide, methacrylic acid, methyl methacrylate or the like. Non-spherical polyacrylate adhesives are commercially available, for example, as the Rohm and Haas Rhoplex™ line of adhesives. Preferably, the non-spherical polyacrylate adhesive is present in an amount of about 10–35% by weight of the total suspension.

Tacky microspheres of adhesive may alternatively be used to help adhere the hydrogel microbeads of the invention to an intended substrate. The tacky microspheres have sufficient adhesive properties to provide the desired adhesive function, yet there is no danger of completely coating the microbead which may lead to potentially inhibiting the release characteristics of the microbead. The combination of microbeads and tacky microspheres may be applied without the need to modify the orifices of conventional sprayers with minimal clogging or plugging problems. Furthermore, the incorporation of tacky (adhesive) microspheres to the (formulation) suspension of microbeads allows the microbeads' surfaces to become tacky. The beads can therefore stick to intended surfaces, such as, foliage and branches, for example. The adhesive microspheres, especially if they are hollow, may also absorb some of the active material into its own body, thus providing a second mechanism of release of the active material. This could result in an overall alteration, preferably an enhancement, of the release profile.

Preferably, the adhesive material is an acrylate- or methacrylate-based adhesive system comprising infusible, solvent dispersible, solvent insoluble, inherently tacky, elastomeric copolymer microspheres as disclosed in U.S. Pat. No. 3,691,140. Alternatively, this adhesive composition may comprise hollow, polymer, acrylate, infusible, inherently tacky, solvent insoluble, solvent dispersible, elastomeric pressure-sensitive adhesive microspheres as disclosed in U.S. Pat. No. 5,045,569. Other suitable adhesives are the tacky microspheres having pendant hydrophilic polymeric or oligomeric moieties that are disclosed in U.S. Pat. No. 5,508,313.

Alternatively, the adhesive comprises between about 60–100% by weight of hollow, polymeric, acrylate, inherently tacky, infusible, solvent-insoluble, solvent dispersible, elastomeric pressure-sensitive adhesive microspheres having a diameter of at least 1 micrometer, and between about 0–40% by weight of a non-spherical polyacrylate adhesive. The hollow microspheres are made in accordance with the teaching of European Patent Application 371,635.

The compositions of the present invention may also include one or more adjuvants including, for example, gelling aids, preservatives, dyes, humectants, fixatives, emulsifiers, extenders, and freeze/thaw stabilizers such as polyhydric alcohols and their esters. These materials are present in an amount effective to achieve their extended function, generally less than about 5% typically less than 2%, by weight of the composition.

Incorporation of a light stabilizer can be included in the microbeads of the invention. Suitable light stabilizers include the tertiary phenylene diamine compounds disclosed in Canadian Patent No. 1,179,682, the disclosure of which is incorporated by reference. The light stabilizer can be incorporated by dissolving it, with the active, in a water-immiscible solvent. Alternatively, a light stabilizer can be incorporated in the microbeads as taught in Canadian Patent No. 1,044,134, the disclosure of which is also incorporated by reference.

The process of making the microbeads of the invention, preferably comprises, initially, the formation of a microemulsion and the dispersion of the active material in the hydrogel material. The microemulsion is then mechanically atomized to create substantially spherical droplets which are subsequently gelled (hardened) to form a hydrogel microbead having an active material dispersed therein.

In a preferred method of making the microbeads of the invention, an emulsion of an oil active within a water soluble solution comprising a hydrogel is first formed. This emulsion is then followed by a mechanical microbead forming step that can be performed by, for example, spray method or emulsification. The droplets are then hardened or cured either by chemical means (i.e., polymer cross-linking) or by non-chemical means (i.e., temperature, pH, pressure). The resulting microbead is a hydrogel microbead, having greater than about 30% water initially, and the active would be finely dispersed and entrained within the water-polymer matrix. The microbeads tend to be more spherical in shape when the spray method is used, as compared to the emulsification method. The size of the microbeads is generally governed by the intrinsic properties of the emulsion solution, the feed rate and the coaxial airflow rate.

The droplets which are atomized can then be allowed to free-fall directly into a reacting bath. The reacting bath cures or sets the hydrogels so that they solidify. Reaction bath curing can be achieved through chemical or non-chemical means. For the case of sodium alginates, calcium ions are used to cross-link the polymer chains. A preferred crosslinker is calcium chloride.

The emulsification method is another technique that can be used for producing hydrogel microbeads. In selecting the continuous phase material, it is preferable that it be immiscible with both the aqueous polymer and oil active.

The matrix-forming material preferably has a range of concentrations usable in practicing the invention. The concentration should be chosen to optimize ease of handling, gelling time, the strength of the hydrogel microbead around the active material droplets. For example, a sodium alginate solution can preferably be prepared in a concentration of about 1 to about 10% (w/v) in water, more preferably about 1.5 to about 5% and most preferably from about 1 to 3%. However, if the hydrogel agent concentration is too great, the solution may be so viscous as to hinder the formation of spherical microbeads.

Alternatively, hydrogel microbeads of the invention can be formed, for example, by adding the matrix forming material solution drop-wise to a selected crosslinker. For example, a method can be used whereby droplet formation and crosslinker addition is completed as a one step process by a vibrating nozzle which ejects a hydrogel droplet from one source and coats the droplet with a crosslinker from another. U.S. Pat. No. 4,701,326 teaches use of this method.

In the preferred aspect where alginates are used to immobilize an active material, a crosslinker is preferably made up in solution at a concentration of 1 to 1000 millimolar, more preferably 20 to 500 millimolar and most preferably from 50 to 100 millimolar. The concentration ranges may have to be adjusted, depending on the nature of a crosslinker and matrix-forming material.

The microbeads containing matrix material and active material can be treated with the crosslinker solution by soaking, spraying, dipping, pouring or any of sever other methods which will deposit an amount of the complexing agent on the droplet. When soaking, the time in solution may be from 1 second to 24 hours, preferably 1 minute to 1 hour, and more preferably from 10 to 30 minutes.

The temperature for hydrogel microbead formation is preferably chosen as to avoid damage or alteration to the active material. For example, in the preferred aspect where alginates are utilized, the temperature is preferably in the range of about 1° C. to about 70° C.; more preferably between about 10° C. to about 40° C., and most preferably between about 15° C. to about 30° C.

Forming the secondary layer of the microbead may be accomplished in various methods. In one aspect, both the secondary layer and the hydrophilic matrix core can be produced substantially simultaneously. In this process, the ionically complexed layer is formed while the crosslinker diffuses into the matrix-forming material to form (gel) the matrix core.

In a preferred method utilizing ionic complexation to form the secondary layer, the active material is emulsified and entrained into the matrix-forming material with the aid of surfactants. The intact beads are then placed into an ionically complexing solution containing opposing charges (either positively or negatively charges), depending on the selection of the hydrophilic matrix forming material for a specified period of time.

The reaction time or the length of incubation time of the secondary layer forming material and the matrix forming material should be sufficient to complex to the hydrogel bead. Preferably, the reaction time is between 5 min to 3 hours, preferably between 5 min and 1 hour, and even more preferably is 30 min.

In a preferred method where in situ polymerized polyurea (PU) membranes are formed as the secondary layer, the polyisocyantes are first dispersed within the matrix forming material and/or along with the active material. The microbeads can then be formed in a crosslinking solution, where the secondary layer is formed substantially simultaneously as the matrix core with active droplets entrained therein.

In another preferred method where in situ polymerized polymethylene urea membranes (PMU) are formed on hydrogel microbeads, the matrix core with active droplets entrained therein is formed prior to forming the secondary layer. The secondary layer is then preferably formed by providing an aqueous solution of a water-soluble, low-molecular weight urea-aldehyde precondensate comprising predominantly low molecular weight reaction products of urea, melamine or thiourea and formaldehyde and adding acid thereto in amount to provide a pH for the dispersion in the range of about 1 to 6.0 and more practically about 1.0 to 3, thereby promoting acid catalysis of the precondensate. Polymerization of the precondensate to a water-insoluble urea-formaldehyde polymer can be continued by agitation within a preferable temperature range of about 20 to about 90° C. for at least about one hour. The polymerized layer can then be neutralized using sodium hydroxide.

Prior to adding the microbeads a suspending solution, the microbeads are preferably washed and filtered using, for example, a Buchner type funnel.

Surfactants can be used in the process of forming the microbeads. The incorporation of different surfactants will offer different types of microemulsion drop sizes of the active within the hydrogel as well as dictate the amount of free oil lost in the reacting bath solution. A preferred surfactant has a high critical micelle concentration, such as for example, a product available under the product designation DISPONIL SUS IC 875 (CMC ~1%)., available from Henkel (Ambler, Pa.).

Particularly preferred surfactants are nonionic. Examples of suitable surfactants include polyvinylpyrrolidone (PVP) and poly(ethoxy)nonylphenol. PVP is usable and available at various molecular weights in the range of from about 20,000 to about 90,000. PVP having a molecular weight of about 40,000 is preferred. Poly(ethoxy)nonylphenols are commercially available under the trade designation IGEPAL from Rhone-Poulenc (Cranbury, N.J.), with various molecular weights depending on the length of the ethoxy chain. Poly(ethoxy)nonylphenols having the formula:

where n has an average value from about 9 to about 13 can be used. A preferred poly(ethoxy)nonylphenols is available commercially under the product name IGEPAL 630, from Rhone-Poulenc (Cranbury, N.J.)—630 is indicative of the approximate molecular weight of the compound. Other examples of suitable surfactants include polyether block copolymers, such as those available under the trade designations PLURONIC and TETRONIC, both available from BASF (Washington, N.J.), polyoxyethylene adducts of fatty alcohols, such as BRIJ surfactants available from ICI (Wilmington, Del.), and esters of fatty acids, such as stearates, oleates, and the like. Examples of such fatty acids include sorbitan monostearate, sorbitan monooleate, sorbitan sesquioleate, and the like. Examples of the alcohol portions of the fatty esters include glycerol, glucosyl and the like. Fatty esters are commercially available as surfactants under the trade designation ARLACEL C from ICI (Wilmington, Del.)

Various properties of the surfactant, such as for example, chain length, functional groups, and hydrophobic regions, can affect the size of the active droplets formed within the microbeads. For example, use of PVP (having a molecular weight of 40,000) tend to result in production of larger sized active droplets than use of poly(ethoxy)nonylphenols (IGEPAL 630).

Ionic surfactants can alternatively be used in the processes of the invention. Examples of suitable ionic surfactants partially neutralized salts of polyacrylic acids such as sodium or potassium polyacrylate or sodium or potassium polymethacrylate.

The active material entrained in the microbeads of the invention are released gradually over time. While not being bound by this theory, it is believed that a mechanism of release of the active in the microbeads of the invention involves water evaporation from the matrix core and then diffusion of active through the secondary layer. In another aspect, the active may be released by entrainment with the hydrogel matrix as the water evaporates, in addition to release by diffusion through the secondary layer. Where multiple layers are optionally included in the microbeads of the invention, the active preferably diffuses though each layer.

In preferred applications, these hydrogel microbeads would be sprayed followed by water evaporation within the gel. As the hydrogel bead dehydrates, the matrix shrinks in size and releases its active with time. The degree of shrinkage of the microbead from its original size, depending on the components used in the formulation. Preferably, the microbeads shrink about 10 to about 90% from its original size, more preferably from about 40 to about 80%, and most preferably from about 50% to about 70%.

Active release from the microbeads of the invention has surprisingly been found to be controllable by controlling the humidity (and dryness) of the environment in which the microbeads are in. Advantageously, the microbead, upon re-exposure to humidity, can swell and rehydrate itself by absorbing water. Re-exposure to humidity can be performed in various ways. For example the microbeads' surfaces can be contacted directly with water or other aqueous solutions. In agricultural applications where pheronomes are used as the active material, a farmer or caretake can irrigate the plants and foliage to re-hydrate the hydrogel microbeads. Alternatively, the humidity of the environment or ambient air in which the microbeads are located in can be increased by entraining air droplets in the air. Thus, the microbeads can be "re-activiated" by re-hydration, thereby selectively controlling the release times of the active material.

It is contemplated that in the preferred embodiment where the microbead comprises a secondary layer ionically complexed to the matrix core surface, swell rates or rehydration effects may result in a further alteration of the release profile of the active. This may be due to the secondary layer having a different absorption rate than that of the hydrophilic matrix core. Advantageously, this can provide extended release profiles of the active to a desired environment.

The microbeads of the invention can be delivered to an intended substrate by various methods. In the preferred embodiment where the active material is a pheromone, delivery of the microbeads will depend on various factors, such as for example, the size of release coverage desired. For small concentrated areas, the microbeads can be impregnated into hollow fibres, plastic laminate flakes or twist-ties and then physically attaching the fibres or ties to plants to be protected from insect infestation. For larger areas, spraying (aerially or by back-pack) may be the better option.

All patents cited in this specification are hereby incorporated by reference.

The following examples are provided to illustrate, but not limit, the scope of the invention. Unless otherwise specified, all parts and percentages are by weight.

EXAMPLES

The following list of materials were used in the Examples. Listed adjacent to each material is the manufacturer and/or supplier from which the materials were obtained.

| | |
|---|---|
| 3M HFE 7100 | 3M Co. (St. Paul, MN) |
| Carvone | Bedoukian (Danbury, CT) |
| Disponil SUS IC 875 | Henkel (Ambler, PA) |
| Drakeol 34 | Penreco (Karns City, PA) |
| E,E-8,10-C12 alcohol | Shin-Etsu Chemical Co., Ltd. (Tokyo, Japan) |
| Igepal C0-630 | Rhone-Poulenc (Cranbury, New Jersey) |
| Menthone | Berjé (Bloomfield, NJ) |
| Paraffin Wax | Aldrich Chemical Co. (Milwaukee, WI) |
| Sodium alginate | SKW (Lannilis, France) |
| Solvent 100 | Shell Chemical Co. (Bayway, NJ) |
| Starch | Aldrich Chemical Co. (Milwaukee, WS) |
| Tixogel EZ100 | Süd-Chemie Rheologicals (Louisville, KY) |
| Z11-C14 acetate | Shin-Etsu Chemical Co., Ltd. (Tokyo, Japan) |

TEST METHODS

To evaluate the physical performance of microbeads of the invention, two parameters were measured: (1) air concentrations of pheromone released from the microbead formulation and (2) the amount of active remaining (i.e., residual concentration) in the microbead over time.

Air Concentration Determination

A known amount of beads (10 microbeads) were recovered and placed in a constant airflow chamber of 100 mL/min (~23–24° C. temperature). The effluent air stream from the chambers was analyzed for active concentration using solid phase microextraction (SPME) (Supelco, Bellefonte, Pa.) and gas chromatography (GC) (Varian Chromatography Systems, Walnut Creek, Calif.) over a period of weeks to evaluate the performance of the hydrogel microbeads.

To calculate the Release Rate of an active, the Air Concentration is multiplied by the Air Flow rate.

Residual Concentration Determination

Formulations were filtered using a Buchner type vacuum funnel, washed with room temperature distilled water and dried in a fumehood at room temperature for 24 hours. Fifty milligrams of the dried formulation were put on tinfoil squares as application substrates. After the required exposure time, the microbeads were subjected to extraction for at least 24 hours with 4 mL of dichloromethane to determine the residual level of active still remaining in the formulation. Each collected sample was then analyzed by gas chromatography.

Example 1

Formation of Pheromone Entrapped Hydrogel Microbeads

For each of the Samples A–J (shown in Table 1), a sodium alginate solution was initially prepared by dissolving a preweighed amount of alginate into a known volume of distilled water. The solution was mixed thoroughly to solubilize the polymer and was deaerated for removal of entrained air bubbles. In a separate 250 mL vessel, the active and surfactant was added and mixed at a speed of about 2000 RPM using a marine type impeller (3.81 cm diamter). To the mixture, the alginate solution was gradually added to form the microemulsion. The emulsion was homogenized for about 30 minutes. The emulsion was then atomized into fine particle droplets using a coaxial air nozzle sprayer. The size of the particles was determined by the settings on the atomizing device. This involved control of the nozzle head diameters, the feed rate of the emulsion through the nozzle and the airflow which passed along its feed path (shown in Table 2). For an example, to create fine particles within the sprayable range (Sample E), the nozzle feed diameter was 0.508 mm, the coaxial air nozzle was 1.4 mm, the feed pressure was about 34.4–110.3 kPa, and the airflow was about 13.8–34.5 kPa. As a result, discrete spherical microbeads were produced with a particle size range of 4 to 400 microns.

Examples A–F demonstrated the ability of this invention to encapsulate oils or pheromones with function groups of ketones, alcohols, and acetates. All the formulations resulted in spherical intact hydrogel microbeads containing the desired active.

Examples G–I demonstrated the ability of this invention to absorb oils or pheromones with functional groups of ketones, alchols, and acetates within an absorbent material prior to encapsulation within a hydrogel matrix. All the formulations resulted in spherical intact hydrogel microbeads containing the desired active.

TABLE 1

Hydrogel microbead formulations

| | Sodium alginate | | Active | | Surfactant | | |
|---|---|---|---|---|---|---|---|
| Sample | Conc. (g/100 mL) | Weight (g) | Type | Weight (g) | Type | Weight (g) | Calcium conc. (mM) |
| A | 2.0 | 50.0 | Carvone | 20.0 | Igepal CO-630 | 2.0 | 50 |
| B | 2.0 | 50.0 | Carvone | 5.0 | Igepal CO-630 | 1.0 | 50 |
| C | 2.0 | 38.6 | E, E-8, 10-C12 alcohol/Solvent 100 (1:4 by wt) | 1.0 | Disponil SUS IC 875 | 1.0 | 50 |
| D | 2.5 | 250.0 | Menthone | 50.0 | Igepal CO-630 | 5.0 | 50 |
| E | 2.5 | 800.0 | Z11-C14 acetate | 20.0 | Igepal CO-630 | 2.0 | 1000 |
| F | 2.0 | 38.6 | Z11-C14 acetate | 1.0 | Disponil SUS IC 875 | 0.4 | 50 |
| G | 2.0 | 40.0 | Z11C14 acetate/ starch (1:4 by wt) | 3.0 | n/a | | 50 |
| H | 2.5 | 250.0 | Menthone/ Tixogel EZ100 (8:1 by wt) | 56.0 | n/a | | 50 |
| I | 2.5 | 250.0 | Menthone/ parrafin wax (10:1 by wt) | 44.0 | n/a | | 50 |

Hydrogel microbeads were formed using coaxial airflow atomization, using the formulations of Samples A and E. Average particle diameters were measured by evaluating 30–50 microbeads, using a stereomicroscope product name STEREOZOOM 7 available from Bausch & Lomb (Brick, N.J.) and a light microscope product LEITZ DIAPLAN available from Ernst Leitz (Wetzlar, West Germany). The nozzle size and settings varied respectively to produce different size particles, as shown in Table 2.

TABLE 2

| Sample | Feed Nozzle | | Coaxial air | | Mean |
| --- | --- | --- | --- | --- | --- |
| | Diameter (in.) | Pressure (psi) | Diameter (in.) | Pressure (psi) | Diameter (mm) |
| A | 0.020 | 10 | 0.046 | 0 | 2.8 |
| | 0.016 | 20 | 0.046 | 0 | 1.7 |
| | 0.020 | 10 | 0.046 | 5 | 0.9 |
| | 0.016 | 20 | 0.046 | 5 | 0.2 |
| E | 0.020 | 5 | 0.055 | 5 | 0.094 |
| | 0.020 | 16 | 0.055 | 2 | 0.135 |
| | 0.020 | 16 | 0.055 | 5 | 0.126 |
| | 0.020 | 14 | 0.055 | 4 | 0.063 |

Example 2

Ionic Complexation to Form Secondary Layer

Example 2A

2 Step Process

The procedure outlined in EXAMPLE 1 was adopted, where Sample E was used, with the variation that a polymer forming solution was used first to crosslink the emulsion droplet on the outside peripherial. In a vessel, a solution of chitosan (Seacure 143, Pronova Biopolymer, Washington) containing 5% glacial acetic acid was prepared by mixing at room temperature. The solution pH was adjusted to about 5.6 using sodium hydroxide. The method of microbead preparation utilizing coaxial air atomization was also adopted using protocol demonstrated in EXAMPLE 1. As an example, the nozzle feed diameter was 0.020 inches, the coaxial air nozzle diameter was 0.055 inches, the feed pressure was about 10 psi, and the airflow was set to 0 psi. After the microbeads were formed, they were soaked in the forming solution for about 3–4 hours. To solidify the membrane bound pheromone droplets, 11 g of calcium chloride crystals were added to the suspension. The microbeads were then gelled for 3–4 hours, filtered and washed with water. As a result of the following example, discrete spherical menthone immobilized hydrogel microbeads were produced with an average particle size of about 2.5 millimeters.

Example 2B:

1 Step Process

The procedure outlined in EXAMPLE 1 was adopted, where SAMPLE A was used, in addition to a polymer forming solution along with the calcium chloride. In a vessel, a solution of chitosan (Seacure 143, Pronova Biopolymer, Washington) containing 1% glacial acetic acid and 50 millimolar calcium chloride was prepared by mixing at room temperature. The solution pH was adjusted to about 5.6 using sodium hydroxide. The method of microbead preparation utilizing coaxial air atomization was also adopted using protocol demonstrated in EXAMPLE 1. The nozzle feed diameter was 0.020 inches, the coaxial air nozzle diameter was 0.055 inches, the feed pressure was about 10 psi, and the airflow was set to 0 psi. As a result of the following example, discrete spherical carvone immobilized hydrogel microbeads were produced with an average particle size of about 3.2 millimeters.

Example 3

In-situ polymerization

Preparation of the prepolymer

A 1 L jacketed reactor set to 71° C. was charged with 326.0 g formaldehyde (Hoechst-Celanese, Rock Hill, S.C.), 121.6 g urea (Arcadian Corporation, Memphis, Tenn.) and 1.14 g potassium tetraborate tetrahydrate (Aldrich Chemical Co., Milwaukee, Wis.). The solution was mixed for 2.5 hours at 350 RPM using a six blade turbine. Dilution water (552.4 g) was then added and mixed well before bottling and storing at room temperature.

Example 3A

The procedure outline in EXAMPLE 1 was adopted, where Sample E was used to produce discrete menthone immobilized in microbeads of about 1 millimeter in diameter. Filtered and water washed microbeads were placed into a 35° C. jacketed reactor charged with distilled, room temperature water (43.86 g) and the prepolymer solution (101.54 g). The suspension was then mixed at about 100 RPM using a six blade turbine for 5 minutes. Gradually, the pH was was adjusted from an initial 8.5 to a final 2.8 using concentrated sulfuric acid (1.2N) at an approximate rate of 0.08 pH units/min. The reaction was stirred at 100 RPM for 30 minutes, before lowering the pH to 2.1 and temperature to 25° C. The reaction was stirred for a further 1 hour, then the temperature was increased to 60° C. over 15 minutes, and the mixture held for a final 1 hour. The reaction mixture was cooled to room temperature and neutralized with ammonium hydroxide. The microbeads were filtered and washed several times with water. The resulting microbeads were discrete and possessed a rigid, hard coating.

Example 3B

The procedure outlined in EXAMPLE 3A was adopted and followed except that the microbeads used were chitosan layered menthone hydrogel microbeads obtained from EXAMPLE 2A. The resulting microbeads were discrete and possessed a secondary layer.

Example 3C

The procedure outline in EXAMPLE 3A was adopted and followed except that the microbeads used were carvone hydrogel microbeads obtained from Sample B. The resulting microbeads were discrete and possessed a secondary layer.

Example 3D

The procedure outline in EXAMPLE 3A was adopted and followed except that the microbeads used were menthone absorbed in clay (Tixogel EZ 100, Süd-Chemie Rheologicals, Louisville, Ky.) calcium alginate hydrogels obtained from Sample I. The resulting microbeads were discrete and possessed a secondary layer Example 3E The pocedure outline in EXAMPLE 3A was adopted and followed except that the microbeads used were menthone absorbed in wax (Paraffin Wax, Aldrich) calcium alginate hydrogels obtained from Sample J. The resulting microbeads were discrete and possessed a secondary layer.

Example 4

Following the test methods described above for Air Concentration, known batches from Sample A and Example 2B were evaluated over a duration of at least 7 weeks while Sample B and Example 3C were evaluated for 5 days. Tables 3 provides the release rate analysis. Air Concentration Determination analysis showed a burst of active (carvone) in the air during the first day followed by a gradual decrease with time for all formulations. In the initial portion of the total release period, the release rate for the microbeads comprising a secondary layer was observed to be significantly lower than that of non-layered microbeads. Subsequently, the longevity of the release is extended significantly as a result of forming an ironically complexed layer on hydrogel microbeads. Similarly, lower release rates were observed for in situ polymerized layers at the initial. This, in turn, increases the longevity of the release.

TABLE 3

| Time (days) | Release rate in air (ng/min per mg carvone) | | | |
|---|---|---|---|---|
| | Sample A No 2$^{nd}$ layer | Example 2B w/layer | Sample B No 2$^{nd}$ layer | Sample 3C w/layer |
| 0 | 165.9 | 144.8 | 601.6 | 72.2 |
| 0.05 | 556.8 | 123.0 | 554.2 | 25.3 |
| 0.08 | 941.2 | 126.3 | — | — |
| 0.12 | 877.5 | 248.9 | — | — |
| 0.15 | 854.2 | 467.8 | 498.6 | 15.3 |
| 1 | — | 141.9 | — | — |
| 2 | 43.3 | 118.7 | 2.1 | 1.1 |
| 5 | 0.001 | 36.2 | 1.0 | 0.5 |
| 8 | — | 0.177 | — | — |
| 10 | 0.001 | 0.089 | — | — |
| 13 | 0.001 | — | — | — |
| 15 | — | 0.026 | — | — |
| 18 | — | 0.016 | — | — |
| 20 | — | 0.017 | — | — |
| 25 | — | 0.011 | — | — |
| 47 | — | 0.007 | — | — |
| 61 | — | 0.004 | — | — |

What is claimed is:

1. A method of delivering and releasing a pheromone comprising the steps of:
   a) providing a bead comprising
      a hydrophilic matrix core having a plurality of pheromone droplets entrained in said matrix core, said core having an outer surface,
      a secondary layer adjacent and ionically complexed to said outer surface; and
      wherein said bead is capable of dehydrating and rehydrating to release the pheromone,
   b) suspending a plurality of said beads in a solution;
   c) delivering said solution comprising said beads to an intended environment; and
   d) allowing said beads to dehydrate.

2. The method according to claim 1 further comprising the steps of:
   e) exposing said beads to humidity; and
   f) allowing said beads to rehydrate.

3. The method according to claim 1 wherein hydrophilic matrix core is an alginate.

4. The method according to claim 1 wherein said hydrophilic matrix core is an alginate.

5. The method according to claim 2 wherein said step of exposing said beads to humidity is performed by wetting the surfaces of said beads with a solution.

6. The method according to claim 2 wherein said steps c) thru e) are repeated sequentially.

7. A method of delivering and releasing a pheromone comprising the steps of:
   a) providing a bead comprising
      a hydrophilic matrix core having a plurality of pheromone droplets entrained in said matrix core, said core having an outer surface,
      a secondary layer adjacent and hydrogen bonded to said outer surface; and
      wherein said bead is capable of dehydrating and rehydrating to release the pheromone,
   b) suspending a plurality of said beads in a solution;
   c) delivering said solution comprising said beads to an intended environment; and
   d) allowing said beads to dehydrate.

8. The method according to claim 7 further comprising the steps of:
   e) exposing said beads to humidity; and
   f) allowing said beads to rehydrate.

9. The method according to claim 7 wherein said hydrophilic matrix core is an alginate.

10. The method according to claim 8 wherein said step of exposing said beads to humidity is performed by wetting the surfaces of said beads with a solution.

11. The method according to claim 8 wherein said step of exposing said beads to humidity is performed by adding moisture to the ambient air.

12. The method according to claim 8 wherein said steps c) thru e) are repeated sequentially.

* * * * *

UNITED STATES PATENT AND TRADEMARK OFFICE
CERTIFICATE OF CORRECTION

PATENT NO. : 6,365,189 B1
DATED : April 2, 2002
INVENTOR(S) : Douglas Quong

It is certified that error appears in the above-identified patent and that said Letters Patent is hereby corrected as shown below:

Column 1,
Line 4, before "subsequent" insert the missing portion as shown on the attached page.

Column 10,
Line 63, delete the word "triethyl amine" and insert in place thereof
-- triethylamine --.

Signed and Sealed this

Twenty-ninth Day of July, 2003

JAMES E. ROGAN
*Director of the United States Patent and Trademark Office*

Field of the Invention

The invention relates broadly to immobilization and release of active material within hydrogel microbeads having a secondary layer. The hydrogel microbeads can be used to immobilize water soluble and water insoluble actives such as oils, fragrances, lubricants, and agricultural chemicals such as pheromones, herbicides, insecticides and pesticides.

Background

Methods of eliminating unwanted pests from orchards, crops and forests frequently entail the use of organophosphate insecticides. Alternative methods involve insect mating disruption, where insect pheromones are used to control pests and protect agricultural crop. In insect mating disruption methods, the mating pheromone plume of a female insect is typically masked with other pheromone point sources. This reduces the likelihood of a male insect finding a female, and subsequently disrupts and reduces larvae production. The insect population of the next generation is thus decreased, as well as potential crop damage.

Conventional sprayable pheromone formulations are generally provided in liquid filled microcapsules containing an active. Typically, the microcapsules have a polyurea membrane that can be formed using an interfacial process involving an isocyanate and an amine. Microencapsulation by this method has been descibed for example in U.S. Patent 4,487,759 (Nesbitt *et al.*, 1984). These polyurea membranes allow actives to be released into the atmosphere for up to a total of 2-3 weeks for most insect pheromones.

Use of interfacial condensation to encapsulate substances such as pharmaceuticals, pesticides and herbicides is taught in U. S. Patent No. 3,577,515. The encapsulation process involves two immiscible liquid phases (typically water and an organic solvent), one being dispersed in the other by agitation, and the